United States Patent
Rimstad (10) Patent No.: US 7,183,404 B1
(45) Date of Patent: Feb. 27, 2007

(54) VACCINE AGAINST ISA VIRUS

(75) Inventor: Espen Rimstad, Oslo (NO)

(73) Assignee: Intervet International B.V., Boxmeer (NL)

( * ) Notice: Subject to any disclaimer, the term of this patent is extended or adjusted under 35 U.S.C. 154(b) by 168 days.

(21) Appl. No.: 09/979,967

(22) PCT Filed: May 29, 2000

(86) PCT No.: PCT/NO00/00179

§ 371 (c)(1),
(2), (4) Date: Mar. 18, 2002

(87) PCT Pub. No.: WO00/72878

PCT Pub. Date: Dec. 7, 2000

(30) Foreign Application Priority Data

May 31, 1999 (NO) ................................ 19992608

(51) Int. Cl.
*C07H 21/00* (2006.01)
*A61K 39/12* (2006.01)

(52) U.S. Cl. ................ 536/23.72; 536/23.1; 424/204.1

(58) Field of Classification Search ............. 424/204.1; 536/23.1, 23.72
See application file for complete search history.

(56) References Cited

U.S. PATENT DOCUMENTS 5,780,448 A * 7/1998 Davis ........................... 514/44
5,981,173 A * 11/1999 Orth et al. ..................... 435/5

FOREIGN PATENT DOCUMENTS

EP 0 839 913 5/1998

OTHER PUBLICATIONS

Corbeil et al. "Evaluation of the protective immunogenicity of the N, P, M, NV and G proteins of infectious hematopoietic necrosis virus in rainbow trout oncorhynchus mykiss using DNA vaccines" Dis Aquat Organ (Dec. 22, 1999) pp. 29-36.*

Falk, K. "Characterization of Infectious Salmon Anemia Virus, an Orthomyxo-Like Virus Isolated from Atlantic Salmon" J. Virol. (Dec. 1997) vol. 71, pp. 9016-9023.*

Krossoy, B. "The Putative Polymerase Sequence of Infectious Salmon Anemia Virus Suggests a New Genus within Orthomyxoviridae" J. Virol. (Mar. 1999) vol. 73, No. 3, pp. 2136-2142.*

Kibenge, F.S.B. "Growth of infectious salmon anemia virus in CHSE-214 cells and evidence for phenotypic differences between virus strains" J. Gen. Virol. (2000) vol. 81, pp. 143-150.*

Eliassen, T.M. "Initial Events in Infectious Salmon Anemia Virus Infection: Evidence for the Requirement of Low-pH Step" J. Virol. (Jan. 2000), vol. 74, No. 1, pp. 218-227.*

Krossoy et al, "The Putative Polymerase Sequence of Infectious Salmon Anemia Virus Suggests a New Genus within the Orthomyxoviridae," *J. of Virology*, vol. 73(3), pp. 2136-2142 (1999).

Falk et al, "Characterization of Infectious Salmon Anemia Virus, an Orthomyxo-Like Virus Isolated from Atlantic Salmon," *J. of Virology*, vol. 71(12), pp. 9016-9023 (1997).

Mjaaland et al, "Genomic Characterization of the Virus Causing Infectious Salmon Anemia in Atlantic Salmon (*Salmo salar* L.): an Orthomyxo-Like Virus in a Teleost," *J. of Virology*, vol. 71(10), pp. 7681-7686 (1997).

Pubmed ID: 10092978; Lovely et al, "First Identification of Infectious Salmon Anaemia Virus in North America With Haemorrhagic Kidney Syndrome".

* cited by examiner

*Primary Examiner*—Stacy B. Chen
(74) *Attorney, Agent, or Firm*—Banner & Witcoff, Ltd.

(57) ABSTRACT

The invention relates to vaccine against infectious salmon anaemia (ISA) virus, DNA sequences endocing immunogenic proteins from ISA virus, diagnostic kit for detection of ISA specific nucleic acid sequences and proteins and exploitation of the ISA virus genome or parts of it as a general model organism.

9 Claims, 1 Drawing Sheet

VACCINE AGAINST ISA VIRUS

FIELD OF THE INVENTION

The present invention concerns a vaccine against infectious salmon anaemia (ISA), nucleotide sequences encoding for immunogenic proteins from ISA virus, in addition to exploitation of the ISA genome or parts of it within biomedicine (model organism), in human medicine as well as in experimental use, and the use within preventive medicine in fish, hereunder diagnostic use for demonstration of ISA specific nucleic acids or proteins.

BACKGROUND OF THE INVENTION

Infectious salmon anaemia (ISA) is a virus disease limited to Atlantic salmon (Salmo salar L.) in cultivation. The disease was diagnosed first time in 1985 in parr (the Bremnes outbreak). The disease has only been found in Atlantic salmon in salt water or salt water added to fresh water. Administrational measures issued by the authorities, as stamping out (and isolation) of affected fish farms followed by disinfection and restrictions on trading/moving of fish in the area have limited the number of outbreaks from the peak around 1990, but in the later years, the disease has increased in extension. Primarily, ISA has been a Norwegian salmon production problem, and in 1998 15 outbreaks were registered. However, during the period 1997–98, ISA was found and verified in Canada (97) and Scotland (98).

The disease is caused by a general infection which among others cause severe anaemia and bleeding lesions. The disease spreads slowly in an infected fish farm, and the mortality can vary from 15 100%. There is no available cure against ISA. The goal of implemented control measures is to minimalise the risk for exposure of ISA virus to the salmon. The demonstration of infection implies stamping out of all fish in an affected fish farm and disinfection of the localities. There is no available vaccine.

Due to the severe economical strains the disease implies to society in general and to the individual fish farmer, a good and secure diagnostic procedure is of importance. Diagnosis of ISA is still based on a combination of macroscopical and microscopical observations of dead/dying fish (pathological/histological investigations). Recently, researchers have had success in growing ISA virus in cell culture (1), which is very time- and resource demanding. An indirect immune fluorescence test for the demonstration of infective material has been developed for the use in tissue sections and tissue impressions (2). A quick-test, —a RT-PCR (reverse transcriptase polymerase chain reaction)—test to demonstrate ISA virus in salmon has been developed as well. It can also be used in ISA infected fish showing no clinical signs of disease (3). This test is ready for the use in the context of diagnosis and mass investigation.

The most likely preventive action against ISA is the development of a vaccine and other influences of the natural defence system in the salmon.

ISA virus contains a negatively charged single-stranded RNA genome of 8 segments. The total size of the segments is 14,5 Kb (1,5×103 base pairs). The virus replicates itself in the nucleus. It is a 100–120 nm enveloped virus with 10 nm peplomers, and it separates itself from the cell membrane by budding. The entrance of ISA virus in cells is pH-dependant. ISA virus harbours hemagglutinating and hemadsorbent abilities (3). All listed features indicate that the virus belongs to the family Orthomyxoviridae, implying an influenza-like virus.

The immune system of salmon share many similar properties with the immune system of mammals. Accordingly, it is possible to draw a number of parallels. Teleosts posses immunocompetent cells such as B- and T-lymphocytes, lymphokines, complement factors and they produce immunoglobulines. Farmed salmon is vaccinated against important bacterial infections. In Norway, vaccines against the IPN virus is also available, but the effect of these vaccines is discussed. The demand for new and more effective vaccines against virus diseases in farmed fish is substantial. DNA-vaccine is an important candidate among vaccine strategies to choose and has been described in various contexts (4). At DNA immunisation against for instance flue virus, protective effects not only directed against the actual antigen variant of the virus used in the vaccine, but also effect against antigenically different virus have been observed (5). This broad immune response can possibly be explained by a good cellular response. It is assumable that a good cellular immune response provides a far better protection against ISA than humoral immune response alone. This is due to the fact that the cellular immune response is directed against a broader range of antigens, and the cellular response is longer-lasting than the humoral response.

The interferon system is also an interesting part of the teleost immune system against influenza-like viruses including ISAV. The interferons induce retardation of virus replication and are of particular importance before the establishment of a specific immune response. Interferon-induced proteins, known as Mx-proteins, are important in the retardation process of influenza-like viruses. For instance, mice lacking functional Mx-genes do not survive influenza infections (6). Mx-genes are also demonstrated in salmon (7), but these do not seem to repress ISA virus sufficiently to prevent disease. The ISA virus has possibly adopted to salmon to such a degree that it may replicate despite the Mx-response of the host. Mx-proteins from human as well as mouse appear to restrict the replication of ISA virus in cell cultures (8).

There is a relatively large degree of homology between Mx-genes from mammals, birds and fish, indicating the severe threat of influenza-like viruses to the species, creating a selection pressure to the benefit of individuals carrying Mx-genes. It is therefore assumable that influenza-like viruses have existed in the marine environment over a substantial period of time. Farming of salmonids in seawater has established conditions for an effective cultivation and distribution of virus, disease outbreaks represent reminders of the existence of influenza-like viruses in the marine environment. A virus reservoir in the marine environment has not yet been identified, thus complicating preventive measures.

Electron microscope studies have demonstrated that ISA virus buds from endothelial cells in blood vessels in several different organs (9). Following experimental challenge tests, virus particles have been identified in most organs, making the disease different from influenza infections in humans where infection usually is limited to the respiratory system. Orthomyxovirus possess 3–4 different surface proteins,; hemagglutinin is regarded to be of particular importance, being responsible for choice of host cell, this due to receptor recognition and thus the binding to the host cell. Hemagglutinin is likely to harbour similar abilities in the ISA virus. Host-cell restricted and surface located protein splitting enzymes (proteases) are necessary to activate the hemagglutinin, making the transport of virus into the cell possible. In this context, the accessibility and tissue distribution of suitable proteases in addition to the accessibility of cellular surface molecules which can act as receptors for ISA virus is of importance. The wide-spread tissue distribution of ISA virus during infection indicates that if the infectibility is dependant on proteolytic activation of virus proteins, this activation is conducted by ordinarily existing proteases. This can partly explain the pathogenicity of the ISA virus which may give up to 100% mortality in certain outbreaks.

Previously, procedures for immunisation of aquatic species by DNA expression systems have been described. See European Patent application no. 839913/964713 (NO). Herein is described the procedure of immunisation using DNA vaccines directed against various aquatic viruses, ISA virus is not described but mentioned in the Norwegian application in claim 11 page 39. Any specific references concerning ISA virus are not mentioned, neither with respect to which gene sequences which may be efficient, nor methods to sequence them.

The difference between human and fish vaccine is limited. Presently, no DNA vaccine is available commercially. The principle is the same, but the application will be different, and of course infective agent. A limited number of vaccines against virus diseases are available in aquaculture production. DNA vaccines represent a new and promising approach in this context. DNA-vaccination implicates administration of antigen-expression vectors which give protein synthesis in situ in tissues in the vaccinated animal. DNA vaccines have experimentally been shown to give protection against influenza virus in mice (close relative to ISA virus) (10, 11, 12, 13). In contrast to recombinant or subunit vaccines, DNA vaccines will mimic attenuated or living, recombinant vaccines due to their possibility to initiate the production of cytotoxic T-cell responses and antibody responses which recognise authentic conformation dependant epitopes. The matrix proteins in orthomyxovirus is by number the predominant protein in the virus particle and has been demonstrated to be of importance to give cross protection (e.g. protection against different strains of influenza-virus which would give reduced protection due to antigen/genetic drift if this was not the case) in mice (14). The matrix protein should therefore be a part of a DNA-vaccine which should protect against ISA virus (5,10).

The traditional fish vaccines are injected intraperitoneally, and an admixture of adjuvance to increase the effect is used. Oil mixtures based on animals/vegetables are mainly used, which may cause severe side effects in the context of peritonitis which may lead to fusions and reduced appetite. DNA vaccines do not demand adjuvance of this kind to be effective. In certain cases, the use of liposomes may increase the effect, but a good response following intracutaneous and intramuscular injections without admixtures is expected. It is also planned to investigate if sufficient effect after dip- or bath vaccination is raised.

MORE DETAILED DESCRIPTION OF THE INVENTION

The present invention relates to a vaccine against ISA virus, characterized in that it embraces cDNA sequences which are complementary to the ISA virus RNA genome and which encode for immunogenic proteins from the virus, DNA sequences which encode at least one matrix protein from the virus and/or DNA sequences which encode matrix protein and/or protein integrated in the virus membrane. The invention also includes DNA sequences which are characterized in that they encode immunogenic proteins from ISA virus, at least one matrix protein from ISA virus, matrix protein and/or another protein integrated in the ISA virus membrane and/or a DNA sequence, characterized in being represented by nucleotide sequences shown in SEQ ID NO: 1, sequences of relatively high degree of similarity to this in addition to parts of it.

A DNA vaccine has been experimentally produced and some vaccine experiments have been carried out. The results indicate that the prototype is promising and has a certain protective effect, but an optimization is still needed.

The invention also includes a vector which contains said DNA sequence, procedure for production of this DNA, the use of this DNA sequence in diagnostic detection of ISA virus specific proteins/nucleic acids, and detection of antibodies directed against immunogenic ISA virus proteins—encoded by the said DNA sequence.

Fish possess an immune system which is relatively similar to what is known from mammals. In salmon, which have survived ISA infection, ISA virus specific antibodies can be detected. The applicant has cloned and sequenced various parts belonging to the ISA virus, encoding virus proteins important for stimulation of the salmon immune system for eventually providing a protective response against ISA. Based on this and in accordance with the invention, a vaccine is produced. The vaccine contains DNA (optimal and determined construction) which provides a protection against ISA disease when administered to salmon. For instance, following injection, cells will engulf DNA from the vaccine and express virus proteins. This induces an immune response which is similar to what happens following a natural infection and thus provides a better protection compared to the response which only is based on inactivated/killed virus or recombinant proteins. The reason for this is that the proteins which are expressed by a DNA vaccine will be processed as cellular proteins and be presented on the cell surface in the context of antigen-presenting molecules, as proteins from intracellular parasites such as viruses.

In addition a RT-PCR-test has been developed for the use in ILA-virus detection in organ material from salmon. In this test primers reacting with ILA-virus sequences, as described in this invention, have been used. Results from all organ material so far tested indicate accordance to other similar test. Such test is meant for use in mass screening in connection with surveillance, moving fishes from one location to another and disease outbreaks.

The sequence which is shown in SEQ ID NO: 1 encodes a polypeptide of 391 amino acids. The molecule weight of this protein and its encoding gene segment is analogues to what is the case for the matrix protein of the influenza virus. In influenza virus, the most numerous protein in the virus particle is the matrix protein which is present as a non-integrated membrane protein located beneath the virus membrane and provides its rigidity and stability.

BRIEF DESCRIPTION OF THE DRAWINGS

FIG. 1. The graphs illustrate the results of vaccination trail using the ISA-klon1-pEGFP-N1 plasmid as the vaccine (Example 10). Two parallel tanks were used, 50 salmon of approximately 25 grams of size, 25 salmon in each tank were injected twice with ISA-klon1-pEGFP-N1 plasmid while 25 salmon were injected twice with a control plasmid, pEGFP-N1. The horizontal axis denotes the number of days after challenge with virulent ISA virus. The vertical axis denotes the number of accumulated dead salmon. In tank A no difference between the control and vaccinated groups was observed, while in tank B a statistically significant difference was found between the control and vaccinated groups.

FIG. 2. The graphs illustrate the results of vaccination trial using the ISA-klon1-pEGFP-N1 plasmid as the vaccine (Example 10). The graph is the same as FIG. 1, but it only illustrates the results observed in tank B. A statistically significant difference was found between the control and vaccinated groups. Compared to tank A there was a delay in tank B before the control injected fish began to die. This could indicate that a prolonged period of time between vaccination and exposure is better.

Example 1

Isolation of the Gene Segments

Cells were harvested from a 175 cm² cell culture flask with SHK-1 cells which had been infected with ISA virus (Glesvaer strain) for 5 days. Cells were washed twice in PBS. mRNA was subsequently extracted with oligo-dT cellulose in accordance with the producer's instructions (mRNA purification kit, Pharmacia, Uppsala, Sweden). mRNA was precipitated with ethanol and diluted in diethyl pyrocarbonate (DEPC) treated water and concentration of mRNA was determined by measuring $OD_{260}$. Totally 1.0 µg mRNA was subsequently used for first strand synthesis by reverse transcription in accordance with the producer's instructions (TimeSaver cDNA Synthesis Kit, Pharmacia). The primer used for this reaction was an oligo-dT primer with a Not I restriction site in the 5'-end. Following the second strand synthesis, a EcoR I adaptor was attached to cDNA using T4 DNA ligase at 16° C. for 2 hours. This cDNA was subsequently cut using Not I and put into a EcoR I/Not I cut pCRII plasmid. The new plasmid containing the insertion was used for the transfection of *E. coli*. Plasmids from transformed bacteria were purified by miniprep procedure and cut by EcoR I/Not I and separated by electrophoresis in an agarose gel. Plasmid insertions were isolated from the gel and purified (Genclean, Bio 101, Vista, Calif., USA) and stored at −20° C. before being used in hybridization reactions.

In the hybridization reactions, total RNA was extracted from ISA infected and non-infected SHK-1 cells. RNA was extracted by using 8.5 ml TRIzol solution (Gibco BRL, Gaithersburg, Md., USA) per 175 cm² cell culture flask following removal of medium and washing of the cells with PBS. This suspension was subsequently removed from the cell culture flask and transferred to a sentrifuge tube. 8.5 ml chloroform was added and sentrifuged for 50 min. at 3,600× g. The water layer was removed and RNA was pelleted by adding 0.7 volume units of isopropanol. The RNA pellet was washed in DEPC-treated 70% ethanol and diluted in 0.5 ml DEPC-$H_2O$. RNA was subsequently denatured using 1 M glyoxal, 10 mM $NaPO_4$ at 50° C. for 1 hour, and 10 µg denatured RNA was used in a 1% agarose gel containing 10 mM $NaPO_4$ as buffer. RNA was subsequently blotted to a nylon membrane (Hybond N+, Amersham, Buckinghamshire, UK) and fixed for 2 hours at 80° C. Hybridization was carried out by $^{32}P$ probe labelling (Rediprime DNA labelling system, Amersham). cDNA from ISA virus infected cell cultures was used as probes. The hybridizations were carried out at 50° C. over night and washed in 2×SSC, 0.1% SDS at room temperature in 2×5 min followed by 0.1×SSC, 0.1% SDS at 68° C. for 2×15 min. Probes which gave positive signals from ISAV-infected SHK-1-cells and no signals from non-infected cells were tested for ISA virus specificity with Southern blot hybridization, where measure was total-DNA from non-infected SHK-1 cells cut with either EcoR I, BamHI or Hind III. These probes were also tested in hybridization reactions in which RNA was extracted from pelleted ISA virus from cell culture media and from ISA infected SHK-1 cells. Previous to pelletation of virus from cell culture supernatant, the medium was sentrifuged at 3,000×g for 30 min and subsequently ISA virus was pelletated at 100,000×g for 3 h. RNA from this pellet was divided in 3 fractions; fraction one was treated with RNaseA, fraction two with RNase free DNase and fraction three remained untreated.

One clone gave positive signals in the hybridization reactions with total RNA from ISA infected SHK-1 cells, and no signals from neither RNA nor DNA from non-infected SHK-1 cells. When pelleted ISA virus was used as target, positive signals were obtained against a gene segment of ca. 1.3 kb. This signal vanished subsequent to treatment of ISA virus pellet with RNaseA, however, treatment with RNase free DNase had no effect.

The present ISA virus specific gene sequence was sequenced in an automatic DNA sequencer, DNA-sequencer (ABI Prism 377, Perkin Elmer Applied Biosystems, Foster City, Calif., USA). The nucleotide sequence is shown in SEQ ID. NO.:1.

ISA virus specific gene segments were subsequently further verified as ISA virus specific by determining the terminal 5' and 3' ends by RACE (rapid amplification and cDNAends). In influenza virus, these 5' and 3' terminal ends are constant between the different segments and also partly complementary between themselves. With respect to the sequences according to present invention, these conserved 5' and 3' ends were identified, this serving as a further verification of the ISA virus specificity.

Example 2

Production of DNA-Constructs for the Expression in Eucaryot Cells

Based on the present sequence for gene segment 7, an open reading frame consisting of 1173 nucleotides is identified. This reading frame will theoretically encode a protein of 391 amino acids with a total molecular weigh of ca. 42.8 kD.

To express the large open reading frame (assumed matrix protein gene) in eucaryotic cells, this gene sequence was cloned into the pEGFP-N1 vector (Clonetech. GenBank accession number U55762). In this vector, the expression of the cloned gene is controlled by a cytomegalovirus promotor, which has been demonstrated to be effective in fish. The expressed protein is a fusion protein between GFP (green fluorescent protein), this is located in the N terminal of the protein, and is therefore expressed only if the pre-encoded protein also is expressed. In short, this is achieved by the following method: Two PCR primers were constructed complementary to each side of the open reading frame, and in addition, each possessed a restriction enzyme site in the 5' terminal (NaeI and kph). The restriction enzymes were chosen from these criteria: a) no restriction sites in the actual gene sequence, b) the restriction site is present in the expression vector.

The PCR primers which were used for amplification of the mentioned open reading frame for subsequent cloning into the pEGFP-N1 vector are shown beneath:

```
PRIMER:    5'-GG-GCT-AGC-ATG-GCA-CGA-TTC-ATA-ATT-TTA-3'
           (SEQ ID NO: 4)
NAME:      KLON1-EGFP-F1
POSISTION: 7-28, KLON1.
DIVERSE:   Starting codon in bold letters. NhaI site is underlined.

PRIMER:    5'-G-GGG-TAC-CGT-AGC-AAC-AGA-CAG-GCT-CGA-TGG-3'

NAME:      KLON1-EGFP-R1
POSITION:  1179-1159, KLON1.
DIVERSE:   Last codon (that is inverse of this codon) previous to stop codon is in
           bold letters. KpnI site is underlined. Two nt (GT) were put in between last codon and
           KpnI to obtain correct reading frame for the GFP protein in the pEGFP N1 vector.
```

Following PCR was performed:
26 µl H$_2$O
5 µl 10×Taq polymerase buffer without MgCl2
8 µl 1.25 mM dNTP
1.5 µl MgCl2
1 µl W-1
1.5 µl KLON1 EGFP-F1 (15 pmol/µl)
1.5 µl KLON1 EGFP-R1(15 pmol/µl)
0.5 µl Taq-polymerase
45 µl totally Subsequently, 5 µl cDNA was produced from RNA which was extracted from organ material from salmon experimentally infected with ISA virus, the Glesvaer strain.
Following PCR was performed:
Initially 5 min at 94° C.
Thereafter 35 cycles with:
30 sec 94° C.
1 min 55° C.
30 sec 72° C.
Thereafter 7 min at 72° C., and 4° indefinitely.

10 µl of the PCR solution was used for electrophoresis in a 2% agarose gel and subsequently stained with ethidium bromide. DNA fragments with correct size according to the open reading frame were cut out from the gel and purified with Geneclean.
DNA from the bit of gel was diluted in 10 µl H$_2$O.
The DNA was subsequently cut by NheI/KpnI
  10 µl DNA from KLON1-EGFP-N1/KLON1-EGFP-R1PCR
  2 µl React 3 (GIBCO buffer for restriction enzymes)
  5 µl H$_2$O
  1 µl NheI
  1 µl Kpn I
  20 µl
Incubated at 37° C. in 2 h.
  1 µl pEGFP-N1
  2 µl React 3 (GIBCO buffer for restriction enzymes)
  15 µl H$_2$O
  1 µl NheI
  1 µl Kpn I
  20 µl
Incubated at 37° C. for 2 h.

Everything was run in electrophoresis in 2% agarose gel and subsequently stained with ethidium bromide. The DNA fragments were cut out and isolated and DNA was extracted (Geneclean). DNA from each of the bits of gel was subsequently diluted in 5 µl H$_2$O. 1 µl of this was used to measure the DNA amount (OD$_{260}$). Relative mass relation ratio between NheI/Kpn I-cut pEGFP-N1 and the PCR amplified NheI/Kpn I-cut DNA-segment was calculated.

Ligation reaction: The mass relation ratio between NheI/Kpn II cut pEGFP-N1 and the PCR amplified, NheI/Kpn I cut DNA segment was in the area of 1:1, 1:3.
  2 µl NheI/Kpn II cut pEGFP-N1
  2 µl NheI/Kpn I cut DNA segment
  1 µl 10×ligase buffer
  4 µl H$_2$O
  1 µl T4 DNA-ligase
  10 µl
Incubated at 16° C. for 4 h.

Fresh, competent *E.coli* cells were transfected in accordance to Maniatis(15).

50 µl and 200 µl from each tube were cultivated on agar plates containing Kanamycin and incubated overnight at 37° C.

5 colonies from these agar plates were used for miniprep of plasmids (Qiagen miniprep). The plasmid pellet was diluted in 20 µl H$_2$O and used in the restriction cutting NheI/Kpn I as this is described previously.

A bacterium clone, which contained plasmid with the correct fragment (ISA klou1-pEGFP-N1) (according to size at electrophoresis), was used for subsequent expression. As backup, 100 µl bacteria solution from the miniprep was spread on agar plates containing Kanamycin, incubated overnight, and the bacterium colonies were diluted in 1 ml LB medium containing 15% glycerol and put in storage at 70° C.

There are also shorter, potential reading frames (see sequence fig.). Influenza virus is the only virus where RNA splicing has been demonstrated, and therefore, similar abilities can not be ruled out in the ISA virus.

Example 3

Amplification of DNA Sequences

The mentioned DNA sequence which is complementary to RNA from gene segment 7 in the ISA virus was amplificated in following ways:

1) PCR using primers complementary to the 5' and 3' terminals of the mentioned sequence. CPR-amplication was used previous to cloning into a vector as described in example 1 and 2, target RNA was then total RNA from an organ from experimentally ISA infected fish, such that possibilities for eventual artificial mutation should remain as little as possible. The PCR requirements used are described in example 2.

2) Amplification of DNA from ISA virus gene segment 7 sequence in the pCRII vector. This sequence lacked the extreme 5' and 3' terminals found using the RACE method (described in example 1). 25 ng of this plasmid (ISA virus gene segment 7-pCRII) was transfected into competent *E.coli* cells (TOP10'). *E.coli* which had been transfected were selected on the basis of resistance against Kanamycin, which is an ability which is encoded by pCRII. Bacterium colonies were tested for plasmid transfection by the aim of miniprep K (Qiagen miniprep). One colony containing the right insertion was cultivated in 5 ml LB medium containing Kanamycin, and the plasmid was purified (Qiagen miniprep). This plasmid was used as DNA source for nucleotide sequencing, which was carried out using an automatic DNA sequencer (as described in example 1).

3) Amplification of DNA which consists of open reading frame insertion in pEGFP-N1 (ILA-klon1-pEGFP-N1).

25 ng of (ILA-klon1-pEGFP-N1) was transfected in *E.coli*. Colonies were selected based on Kanamycin resistance. Thereafter testing for content of correct insertion was performed by miniprep (Qigaen miniprep) and restriction enzyme analysis (NheI/KpnI cutting as described in example 2). A colony of *E.coli* containing plasmid with correct insertion was used for amplification of ILA-klon1-pEGFP-N1. Qiagen Maxiprep and Gigaprep were used for this purpose according to manufacture's instructions.

Example 4

Expression in a Cell Line

The ILA-klon1-pEGFP-N1 plasmid was transfected into BF-2 cells. BF-2 cells represent a standard fish cell line. These were cultivated in 96-well plates following standard procedures. FuGene (Boehringer-Mannheim) transfection medium was used. 1,4 µg DNA was sufficient for 25 wells. Totally 4 µg FuGene/DNA solution was added to each well. The wells contained medium and the cells were not washed or treated in any other way in the process of transfection. The success of transfection was measured by examining the transfected cells in a UV light examination microscope. UV light positive cells would indicate production of GFP (green fluorescent protein), the reading frame for this protein is located downstream of the cloned, open reading frame of the ISA virus segment 7, and will only be expressed in the case of expression of this protein. Expected molecular weight of this fusion protein is 69,7 kD:

| | |
|---|---|
| IIa-Klon1 protein: | Molecular weight = 42.8 kD |
| GFP: | Molecular weight = 26.9 kD |
| Fusion protein: | Molecular weight = 69.7 kD |

The BF-2 cells were examined daily for presence of fluorescene. In a great number of the BF-2 cells, fluorescence was clearly visible, mainly localised to cytoplasm.

Example 5

Expression in Salmon

We want to examine the expression of the open reading frame protein in salmon as described for BF-2 cells in example 4. Partly, material from the immunised fish in example 6 may be used, but other application methods will also be applied. Following injection, samples from the site of injection will be removed, and following the use of for example gene gun, (Gene-gun, BioRad), it will be sufficient to scrape skin etc. Other possibilities will be taken to consideration accordingly. Performed tests will either be Western blotting or examination of fluorescence which detect presence of GFP.

Example 6

Immunisation of Salmon

15 µg of the ILA-klon1-pEGFP-N1 plasmid disolved in 25 µl $H_2O$ was injected intramuscularily in salmon with the size of 40–60 g. Insulin injection devise was used for the injection. A total number of 150 individuals were immunised. The fish were injected only once, i.e. no booster injection was administered.

Example 7

Vaccine Experiments Followed by Exposure to Live ISA Virus (Challenge)

In challenge experiments, individuals with a weight of 40–60 g were immunised with the ILA-klon1-pEGFP-N1 plasmid as described in example 6. Control individuals were immunised with the pEGFP-N1 plasmid devoid of insertion in the same amount and volume as the individuals given the ILA-klon1-pEGFP-N1 plasmid.

Following this immunisation, 4 weeks passed before the salmon was exposed to live ISA virus.

Exposure to ISA virus was performed by co-habitantly infection of the immunised salmons with ISA virus infected salmon.

Experimental ISA infection was performed by injecting salmon with the weight of 40–60 g intraperitoneally with ISA virus from cell culture supernatant diluted 1:10 in cell culture medium. The virus strain was Glesvaer. Virus titre was $10^4$/mL. Injection dosage: 0,3 mL intraperitoneally.

Subsequently, salmon with different immunisation/infection was distributed in the following way:

| | |
|---|---|
| Tank A: | 25 fish vaccinated with Klon1-pEGFP-N1<br>25 fish vaccinated with pEGFP-N1<br>5 experimentally ISA virus infected fish introduced after 4 weeks |
| Tank B: | 25 fish vaccinnated with Klon1-pEGFP-N1<br>25 fish vaccinated with pEGFP<br>5 experimentally ISA virus infected fish introduced after 4 weeks |
| Tank C: | 100 fish vaccinated with Klon1-pEGFP-N1<br>5 experimentally ISA virus infected fish introduced after 4 weeks |
| Tank D: | 100 fish vaccinated with pEGFP-N1<br>5 experimentally ISA virus infected fish introduced after 4 weeks |

Thereafter, status between dead and surviving fish is made after 4–6–8 weeks.

Example 8

Vaccine Effect in Challenge Experiments

It is expected that degrees of protection against ISA infection may be detected. Any kind of protection will be regarded as a positive result. In the experiment, the fish is exposed to a very high transmission pressure, probably higher compared to natural exposure. Over a period of time, one cannot expect the fish to be protected. Therefore, delay of clinical signs of disease compared to control fish will also be regarded as a positive result.

The results of the challenge tests gave no significant difference between vaccinated and control groups.

Example 9

Vaccine Experiments Using Inter Alia Scaled Infection Pressure

Subsequently to example 6–8, new vaccine experiments will be performed. The experiments will be carried out likewise as mentioned, but here with optimalisation regarding either/or application methods or/and type and amount of infection pressure.

Regarding applications, intracutaneous injection using gene gun (BioRad) will be valuated together with bath/dip. Regarding infection amount, one wish primarily to reduce the infection pressure in various ways, for example by reducing amount of experimentally infected fish or by reducing exposure period in the experiment.

Example 10

Vaccine Experiment Repeated as in Examples 6–9 with Some Modifications

Figure 1:
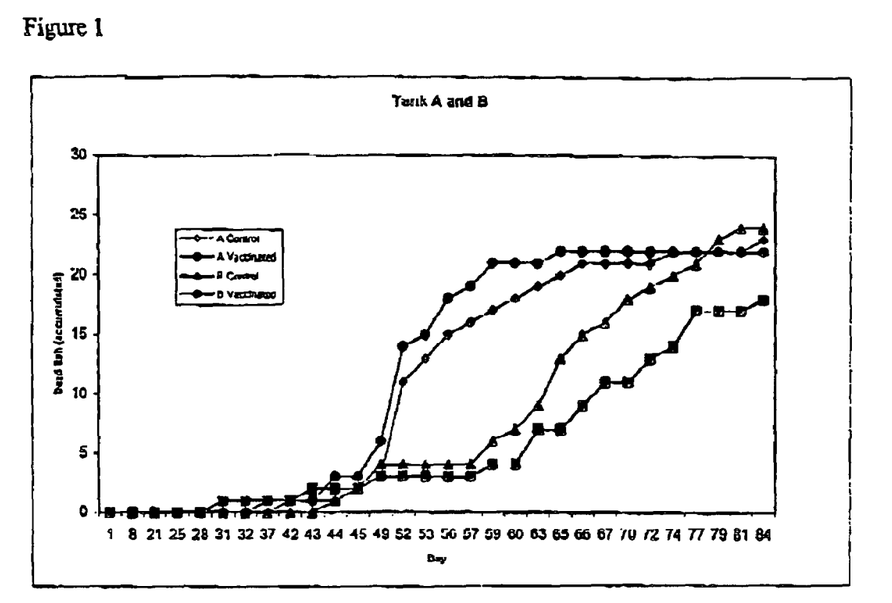
Figure 2:
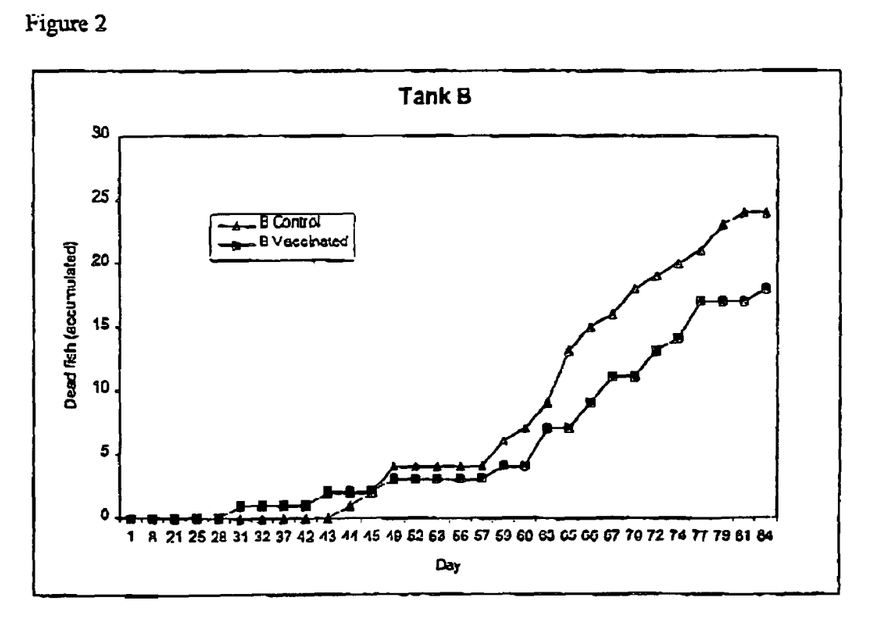

The fish were somewhat smaller than 25 g and were injected with 25 µg of the ILA-klon1-pEGFP N1 plasmid diluted in 100 µl TE with 2% polyvinylpyrrolidon-40. The fish were immunised twice with a 25 days interval. Only the experiments in tank A and B from example 7 were carried out. In tank A, the fish died rapidly, and there was not detected any difference between the groups. On the contrary, in tank B, the mortality was delayed. This may indicate a delayed infection impact compared to the expected 40 days. The experiment was terminiated after ca. 17 weeks. In tank B, a significant difference between the groups was registered, this means that there were more survivors within the vaccinated groups. Using the $X^2$ test, a value of 5.36 was estimated which was significant at $p<0.025$. The values used in the estimations originated from the termination of the experiment, at which point 24 and 18 individuals in the groups of 25 were dead, in which 18 originated from the groups of vaccinated fish.

These results may indicate that a prolonged period of time between vaccination and exposure would have been better experimentally because protection against infection was somewhat more delayed than expected. In other words, the immune system of the fish needs somewhat longer time following DNA vaccination to achieve a good protective response.

Example 11

Identification of ISA Virus

Organ material from ISA infected and non-infected salmon was homogenised, and a RNA extraction was carried out in accordance with commonly known biotechnological methods. Subsequently, Ready-To and RT-PCR Bead (Pharmacia) in the RT-PCR procedure was used. The reverse transcription and PCR reactions were performed as described by the manufacturer. PCR cycle using ISA primers is 95° C. 30 s, 55° C. 15 s and 72° C. 30 s, 35 cycles totally. Primers reacting with ISA virus sequences in accordance to claim 1–6 (labelled 1A and 1B) were used and compared to primers (labelled ILA1 and ILA2) reacting with ISA virus sequences and which are used for diagnostic purposes today. To visualise the reaction, a 3% NuSieve agarose in 1×TAE buffer was used for electrophoresis at 80 volts in 75 minutes, a 123 bp ladder was used as size standard. The gel was put on an UV table and photo was taken.

35 samples from The Norwegian School of Veterinary Science (NSVS) and 54 samples from Scotland were tested. All samples from NSVS tested positively with respect to presence of ISA virus, and the Scottish samples tested negatively. The results show that the sequences mentioned in claim 1–6 with fitting primers are well suited for diagnostic purposes.

SEQUENCE LIST

SEQ ID. NO.:1

The actual sequence corresponds to assumed gene segment 7 in the ISA virus.

Total length is 1320 nucleotides.

The sequence in this gene segment printed in the 5' to 3' direction is:

```
  1 AGUAAAAAAU GCACUUUUCU GUAAACCUAC AACAUCAAGA ACGU-
    CUUCAA

51 CCAAAAACAA UUUUACAUAC AUCUUUAAAA UUAAAAUCAC AUUA-
    GAAUAC

101 ACUCAUUAAC UUUUAACAUA GUUGCUUUUC UUUCAUAAUU AAG-
    CAACAGA

151 CAGGCUCGAU GGUGGAAUUC UACCUCUAGA CUUGUACAUC
    AAUGCUGCAA

201 UCCAAAUACA UGCUUUCCAA CCUGCUAGGA ACAGAGCAAU
    CCCAAAACCU

251 GCUACACCCA UAGUUUGGUU CAGCUGAGGU GGGAUUGCGU CUAC-
    CCUGAU

301 CUUUACAUCU GUGAUGUUCC UCUGAAGUUU ACUGAUCAUC UCCU-
    UAUGCA

351 AUGCUACCUC CCUCAUGAUA AGUGUGUCUG UGUUACCUAA GCU-
    UGUCUGG

401 UCAAAAUCUU UAACCAUCUU AGGGCAGCUG UCAUAUUCAC
    ACGAAGCAGC
```

-continued

```
 451 AUCAAUUCUA CUCCAGUCAA UGUCUGGGCA UGUCAAUGCA
     UCAGUGAGGA

501 ACGUUCUAAC GGAAGCUGAA CCAUGUACUC AGUCAAAACC AUCA-
     GAAGGA

551 UAAACACCCC CUGUAUUUGG UGUGUCUACA UACUCAUCUA GCU-
     CAACGUU

601 CCUCAUGAUG UCUGAACACA AAGGCGUAUC ACUAGAAGAU CUUAG-
     CAGAA

651 CACACUUGUU UUUGGUUCCC CUCACUUCAA AGGUGUCUGA CACCUA-
     GAUU

701 UGUCCUUGGA AAUUGUCAAA CCUCAAAGGU GUGUUGAAAU ACCCG-
     CAUCC

751 GUUGAUCAGU UUCACUCCUC CCACAUUCCC AGAUGUUGCU
     GCAAUGCAGA

801 CCUUGUAGAU UCCGGACAUU CCAUUCAAUC CAACCACUAC AAUU-
     GUAGGG

851 CUGCUGAAAG UCAACACCUU CACCGAAAAA CCGGUAACUG CGUCU-
     GUUCG

901 UCCAACAAGU CCAACAAUUG CUGCUCCCAC AAAUGUAGGC GUCACU-
     CUCA

951 CGUCUCCCCU GCAUGCUCCC AGGUACAGCU CCCUUGCCGC GUUGUC-
     CAGU

1001 GUCAUCGAAG UUGGGAUGAU CAUGUCACUA GGUCCGUCAG
     UGCAGUCAUU

1051 GGUUCCCAAG UAUAGGAUCC GGUACUUUGU AGUAGGUGUG UAC-
     CAGUCAC

1101 UUGGAAACCU UCCACUCAUC UGCUUCAAGA GUCCAUUCC GUU-
     UUUGGCC

1151 UGCAGCACCC CCUUGAACUC AGUCACCAGA UCCAAAGACU GUGGA-
     UUCAC

1201 UCUAGACUGA UCGCUUCGAG AGUCACCUAU CCAGGUGGUG
     UCAGGGUAGU

1251 UUCUAAGACA UAGACGACUG UAAACAGGCG CCAACAGUAG
     GAAUAAAAUU

1301 AUGAAUCGUG CCAUCUUUGC
```

Originally, the gene segment was cloned as mRNA.

Naturally, occurrence of this gene segment is as RNA with negative sense, that is opposite sense of mRNA which per definition is positively sensed. The listed sequence encodes therefore not per se virus proteins, but it has to be transcribed to positive sense initially.

The sequence to positive sense, and re-written to DNA (U to T) is SEQ ID NO 2:

```
  1 CCAAAGATGG CACGATTCAT AATTTTATTC CTACTGTTGG CGCCTGTTTA
 51 CAGTCGTCTA TGTCTTAGAA ACTACCCTGA CACCACCTGG ATAGGTGACT
101 CTCGAAGCGA TCAGTCTAGA GTGAATCCAC AGTCTTTGGA TCTGGTGACT
151 GAGTTCAAGG GGGTCCTGCA GGCCAAAAAC GGAAATGGAC TCTTGAAGCA
201 GATGAGTGGA AGGTTTCCAA GTGACTGGTA CACACCTACT ACAAAGTACC
251 CCATCCTATA CTTGGGAACC AATGACTGCA CTGACGGACC TACTGACATG
301 ATCATCCCAA CTTCGATGAC ACTGGACAAC GCGGCAACGG AGCTGTACCT
351 GGGAGCATGC AGGGGAGACG TGAGAGTGAC GCCTACATTT GTGGGAGCAG
401 CAATTGTTGG ACTTGTTGGA CGAACAGACG CAGTTACCGG TTTTTCGGTG
451 AAGGTGTTGA CTTTCAGCAG CCCTACAATT GTAGTGGTTG GATTGAATGG
```

-continued

```
 501 AATGTCCGGA ATCTACAAGG TCTGCATTGC AGCAACATCT GGGAATGTGG

551 GAGGAGTGAA ACTGATCAAC GGATGCGGGT ATTTCAACAC ACCTTTGAGG

601 TTTGACAATT TCCAAGGACA AATCTACGTG TCAGACACCT TTGAAGTGAG

651 GGGAACCAAA AACAAGTCTC TTCTGCTAAG ATCTTCTAGT GATACGCCTT

701 TGTGTTCACA CATCATGAGG AACGTTGAGC TAGATGAGTA TGTAGACACA

751 CCAAATACAG GGGGTGTTTA TCCTTCTGAT GGTTTTGACT CACTACATGG

801 TTCAGCTTCC GTTAGAACGT TCCTCACTGA TGCATTGACA TGCCCAGACA

851 TTGACTGGAG TAGAATTGAT GCTGCTTCGT GTGAATATGA CAGCTGCCCT

901 AAGATGGTTA AACATTTTGA CCAGACAAGC TTAGGTAACA CAGACACACT

951 TATCATGAGG GAGGTAGCAT TGCATAAGGA GATGATCAGT AAACTTCAGA

1001 GGAACATCAC AGATGTAAAG ATCAGGGTAG ACGCAATCCC ACCTCAGCTG

1051 AACCAAACTA TGGGTGTAGC AGGTTTTGGG ATTGCTCTGT TCCTAGCAGG

1101 TTGGAAAGCA TGTATTTGGA TTGCAGCATT CATGTACAAG TCTAGAGGTA

1151 CAATTCCACC ATCGAGCCTG TCTGTTGCTT AATTATGAAA GAAAAGCAAC

1201 TATGTTAAAA GTTAATGAGT GTATTCTAAT GTGATTTTAA TTTTAAAGAT

1251 GTATGTAAAA TTGTTTTTGG TTGAAGACGT TCTTGATGTT GTACGTTTAC

1301 AGAAAAGTGC ATTTTTTACT
```

The distribution to nucleotides in this sequence is:
A: 375 (28.4%) C: 249 (18.8%) G: 332 (25.2%) T: 364 (27.6%)

This sequence encodes following expected proteins SEQ. ID NO 3:

Start is nucleotide 7, stop after nucleotide 1183.

```
  1 MARFIILFLL LAPVYSRLCL RNYPDTTWIG DSRSDQSRVN DQSLDLVTEF

51 KGVLQAKNGN GLLKQMSGRF PSDWYTPTTK YRILYLGTND CTDGPTDMTT

101 PTSMTLDNAA RELYLGACRG DVRVTPTFVC AAIVGLVGRT DAVTGFSVKV

151 LTFSSPTIVV VGLNGMSGTY KVCIAATSGN VGGVKLINGC GYFNTPLRFD

201 NFQGQIYVSD TFEVRGTKNK CVLLRSSSDT PLCSHIMRNV ELDEYVDTPN

251 TGGVYPSDGF DSLHGSASVR TFLTDALTCP DIDWSRIDAA SCEYDECPKM

301 VKDFDQTSLG NTDTLIMREV ALHKEMISKL QRNITDVKIR VDAIPPQLNQ

351 TMGVAGFGIA LFLAGWKACI WIAAFMYKSR GRIPPSSLSV A*
```

Molecular weight=42755.68 Residues—391
Average Residue Weight=109.350 Charged=2
Isoelectric point—7.66
Extinction coefficient=45750

| Residue | Number | Mole Percent |
|---|---|---|
| A = Ala | 24 | 6.138 |
| B = Asx | 0 | 0.000 |
| C = Cys | 11 | 2.813 |
| D = Asp | 28 | 7.161 |
| E = Glu | 8 | 2.046 |
| F = Phe | 17 | 4.348 |
| G = Gly | 33 | 8.440 |

-continued

| Residue | Number | Mole Percent |
|---|---|---|
| H = His | 3 | 0.767 |
| I = Ile | 24 | 6.138 |
| K = Lys | 16 | 4.092 |
| L = Leu | 36 | 9.207 |
| M = Met | 11 | 2.813 |
| N = Asn | 17 | 4.348 |
| P = Pro | 19 | 1.859 |
| Q = Gln | 10 | 2.558 |
| R = Arg | 22 | 5.627 |
| S = Ser | 31 | 7.928 |
| T = Thr | 32 | 8.184 |
| V = Val | 31 | 7.928 |

-continued

| Residue | Number | Mole Percent |
| --- | --- | --- |
| W = Trp | 5 | 1.279 |
| Y = Tyr | 13 | 3.325 |
| Z = Glx | 0 | 0.000 |
| A + G | 57 | 14.578 |
| S + T | 63 | 16.113 |
| D + E | 36 | 9.207 |
| D + E + N + Q | 63 | 16.113 |
| H + K + R | 41 | 10.486 |
| D + E + H + K + R | 77 | 19.693 |
| I + L + M + V | 102 | 26.087 |
| F + W + Y | 35 | 8.951 |

REFERENCES

1. Dannevig, B. H., Falk, K., and Namork, E. Isolation of the casual virus of infectious salmon anaemia (ISA) in a long-term cell line from Atlantic salmon head kidney. *J.Gen.Virol.* 76(Pt 6):1353–1359, 1995.
2. Falk, K. and Dannevig, B. H. Demonstration of infectious salmon anaemia (ISA) viral antigens in cell cultures and tissue sections. *Vet.Res.* 26(5–6):499–504, 1995.
3. Mjaaland, S., Rimstad, E., Falk, K., and Dannevig, B. H. Genomic characterization of the virus causing infectious salmon anemia in Atlantic salmon (Salmo salar L.): an orthomyxo-like virus in a teleost. *J.Virol.* 71(10):7681 7686, 1997.
4. Leong, J. C., Anderson, E., Bootland, L. M., Chiou, P. W., Johnson, M., Kim, C., Mourich, D., and Trobridge, G. Fish vaccine antigens produced or delivered by recombinant DNA technologies. *Dev.Biol.Stand.* 90:267–77:267–277, 1997.
5. Donnelly, J. J., Friedman, A., Ulmer, J. B., and Liu, M. A. Further protection against antigenic drift of influenza virus in a ferret model by DNA vaccination. *Vaccine* 15(8):865–868, 1997.
6. Amheiter, H., Skuntz, S., Noteborn, M., Chang, S., and Meier, E. Transgenic mice with intracellular immunity to influenza virus. *Cell* 62(1):51–61, 1990.
7. Robertsen, B., Trobridge, G., and Leong, J. A. Molecular cloning of double-stranded RNA inducible Mx genes from Atlantic salmon (Salmo salar L.) [In Process Citation]. *Dev.Comp.Immunol.* 21(5):397–412, 1997.
8. Rimstad, E. Teig, A. :Personal information.1998
9. HOVLAND, T., Nylund, A., WATANABE, K., and ENDRESEN, C. Observation of infectious salmon anemia virus in Atlantic salmon, Salmo-salar L. *JOURNAL OF FISH DISEASES* 17(3):291–296, 1994.
10. Ulmer, J. B., Donnelly, J. J., Parker, S. E., Rhodes, G. H., Felgner, P. L., Dwarki, V. J., Gromkowski, S. H., Deck, R. R., DeWitt, C. M., and Friedman, A. Heterologous protection against influenza by injection of DNA encoding a viral protein [see comments]. *Science* 259(5102):1745–1749, 1993.
11. Fynan, E. F., Robinson, H. L., and Webster, R. G. Use of DNA encoding influenza hemagglutinin as an avian influenza vaccine. *DNA Cell Biol.* 12(9):785–789, 1993.
12. Raz, E., Carson, D. A., Parker, S. E., Parr, T. B., Abai, A. M., Aichinger, G., Gromkowski, S. H., Singh, M., Lew, D., and Yankauckas, M. A. Intradermal gene immunization: the possible role of DNA uptake in the induction of cellular immunity to viruses. *Proc.Natl.Acad.Sci.U.S.A.* 91(20):9519–9523, 1994.
13. Donnelly, J. J., Ulmer, J. B., and Liu, M. A. Protective efficacy of intramuscular immunization with naked DNA. *Ann.N.Y.Acad.Sci.* 772:40–6:40–46, 1995.
14. Webster, R. G. og Hinshaw, V. S. Matrix protein from influenza A virus and its role in cross-protection in mice. Infect.Immun. 17(3):561 566, 1977.
15. Sambrok, J., Fritsch, E. F., og Maniatis, T. Molecular cloning. A laboratory manual, New York: Cold spring harbor laboratory press, 1989.

The invention claimed is:

1. An isolated and purified polynucleotide molecule encoding a polypeptide comprising the amino acid sequence shown in SEQ ID NO: 3.

2. The polynucleotide molecule of claim 1 which comprises nucleotides 7 to 1183 of SEQ ID NO:2.

3. The polynucleotide molecule of claims 1 or 2 which is cDNA.

4. A vector comprising:
a polynucleotide which encodes a polypeptide comprising the amino acid sequence shown in SEQ ID NO: 3, wherein the polynucleotide is a DNA polynucleotide; and
a promoter which controls expression of the polynucleotide, wherein the promoter is located 5' to the polynucleotide.

5. The vector of claim 4 wherein the polynucleotide comprises nucleotides 7 to 1183 of SEQ ID NO: 2.

6. A method of making an expression construct for a polypeptide of an infectious salmon anaemia (ISA) virus comprising:
inserting a polynucleotide comprising the sequence shown in SEQ ID NO:1 or SEQ ID NO:2 into a plasmid, wherein the plasmid comprises a promoter to control expression of the polynucleotide.

7. A vaccine composition comprising an isolated polynucleotide encoding the polypeptide as shown in SEQ ID NO:3.

8. The vaccine composition of claim 7 wherein the polynucleotide comprises nucleotides 7 to 1183 of SEQ ID NO:2.

9. The vaccine composition of claim 7 or 8 wherein the polynucleotide is cDNA.

* * * * *

SEQUENCE LISTING

```
<160> NUMBER OF SEQ ID NOS: 5

<210> SEQ ID NO 1
<211> LENGTH: 1320
<212> TYPE: RNA
<213> ORGANISM: Infectious salmon anemia virus

<400> SEQUENCE: 1
aguaaaaaau gcacuuuucu guaaacguac aacaucaaga acgucuucaa ccaaaaacaa      60
uuuuacauac aucuuuaaaa uuaaaaucac auuagaauac acucauuaac uuuuaacaua    120
guugcuuuuc uuucauaauu aagcaacaga caggcucgau gguggaauuc uaccucuaga    180
cuuguacaug aaugcugcaa uccaaauaca ugcuuuccaa ccugcuagga acagagcaau    240
cccaaaaccu gcuacaccca uaguuugguu cagcugaggu gggauugcgu cuacccugau    300
cuuuacaucu gugauguucc ucugaaguuu acugaucauc uccuuaugca augcuaccuc    360
ccucaugaua agugugucug uguuaccuaa gcuugucugg ucaaaaucuu uaaccaucuu    420
agggcagcug ucauauucac acgaagcagc aucaauucua cuccagucaa ugucugggca    480
```

-continued

| | |
|---|---|
| ugucaaugca ucagugagga acguucuaac ggaagcugaa ccauguagug agucaaaacc | 540 |
| aucagaagga uaaacacccc cuguauugg uguguucuaca uacucaucua gcucaacguu | 600 |
| ccucaugaug ugugaacaca aaggcguauc acuagaagau cuuagcagaa cacacuuguu | 660 |
| uuugguuccc cucacuucaa aggugucuga cacguagauu uguccuugga aauugucaaa | 720 |
| ccucaaaggu guguugaaau acccgcaucc guugaucagu uucacuccuc ccacauuccc | 780 |
| agauguugcu gcaaugcaga ccuuguagau uccggacauu ccauucaauc caaccacuac | 840 |
| aauuguaggg cugcugaaag ucaacaccuu caccgaaaaa ccgguaacug cgucuguucg | 900 |
| uccaacaagu ccaacaauug cugcucccac aaauguaggc gucacucuca cgucuccccu | 960 |
| gcaugcuccc agguacagcu cccuugccgc guuguccagu gucaucgaag uugggaugau | 1020 |
| caugucagua gguccgucag ugcagucauu gguucccaag uauaggaucc gguacuuugu | 1080 |
| aguaggugug uaccagucac uuggaaaccu uccacucauc ugcuucaaga guccauuucc | 1140 |
| guuuuuggcc ugcagcaccc ccuugaacuc agucaccaga uccaaagacu uggauuacu | 1200 |
| ucuagacuga ucgcuucgag agucaccuau ccaggugug ucaggguagu uucuaagaca | 1260 |
| uagacgacug uaaacaggcg ccaacaguag gaauaaaauu augaaucgug ccaucuuugc | 1320 |

<210> SEQ ID NO 2
<211> LENGTH: 1320
<212> TYPE: DNA
<213> ORGANISM: Infectious salmon anemia virus

<400> SEQUENCE: 2

| | |
|---|---|
| gcaaagatgg cacgattcat aattttattc ctactgttgg cgcctgttta cagtcgtcta | 60 |
| tgtcttagaa actaccctga caccacctgg ataggtgact ctcgaagcga tcagtctaga | 120 |
| gtgaatccac agtctttgga tctggtgact gagttcaagg gggtgctgca ggccaaaaac | 180 |
| ggaaatggac tcttgaagca gatgagtgga aggtttccaa gtgactggta cacacctact | 240 |
| acaaagtacc ggatcctata cttgggaacc aatgactgca ctgacggacc tactgacatg | 300 |
| atcatcccaa cttcgatgac actggacaac gcggcaaggg agctgtacct gggagcatgc | 360 |
| aggggagacg tgagagtgac gcctacattt gtgggagcag caattgttgg acttgttgga | 420 |
| cgaacgacg cagttaccgg tttttcggtg aaggtgttga cttcagcag ccctacaatt | 480 |
| gtagtggttg gattgaatgg aatgtccgga atctacaagg tctgcattgc agcaacatct | 540 |
| gggaatgtgg gaggagtgaa actgatcaac ggatgcgggt atttcaacac accttgagg | 600 |
| tttgacaatt tccaaggaca aatctacgtg tcagacacct tgaagtgag ggaaccaaa | 660 |
| aacaagtgtg ttctgctaag atcttctagt gatacgcctt tgtgttcaca catcatgagg | 720 |
| aacgttgagc tagatgagta tgtagacaca ccaaatacag ggggtgttta tccttctgat | 780 |
| ggttttgact cactacatgg ttcagcttcc gttagaacgt tcctcactga tgcattgaca | 840 |
| tgcccagaca ttgactggag tagaattgat gctgcttcgt gtgaatatga cagctgccct | 900 |
| aagatggtta agattttga ccagacaagc ttaggtaaca cagacacact tatcatgagg | 960 |
| gaggtagcat tgcataagga gatgatcagt aaacttcaga ggaacatcac agatgtaaag | 1020 |
| atcagggtag acgcaatccc acctcagctg aaccaaacta tgggtgtagc aggttttggg | 1080 |
| attgctctgt tccagcagg ttggaaagca tgtatttgga ttgcagcatt catgtacaag | 1140 |
| tctagaggta gaattccacc atcgagcctg tctgttgctt aattatgaaa gaaaagcaac | 1200 |
| tatgttaaaa gttaatgagt gtattctaat gtgattttaa ttttaaagat gtatgtaaaa | 1260 |
| ttgttttttgg ttgaagacgt tcttgatgtt gtacgtttac agaaagtgc attttttact | 1320 |

<210> SEQ ID NO 3
<211> LENGTH: 391
<212> TYPE: PRT
<213> ORGANISM: Infectious salmon anemia virus

<400> SEQUENCE: 3

```
Met Ala Arg Phe Ile Ile Leu Phe Leu Leu Ala Pro Val Tyr Ser
1               5                   10                  15

Arg Leu Cys Leu Arg Asn Tyr Pro Asp Thr Thr Trp Ile Gly Asp Ser
                20                  25                  30

Arg Ser Asp Gln Ser Arg Val Asn Pro Gln Ser Leu Asp Leu Val Thr
            35                  40                  45

Glu Phe Lys Gly Val Leu Gln Ala Lys Asn Gly Asn Gly Leu Leu Lys
    50                  55                  60

Gln Met Ser Gly Arg Phe Pro Ser Asp Trp Tyr Thr Pro Thr Thr Lys
65                  70                  75                  80

Tyr Arg Ile Leu Tyr Leu Gly Thr Asn Asp Cys Thr Asp Gly Pro Thr
                85                  90                  95

Asp Met Ile Ile Pro Thr Ser Met Thr Leu Asp Asn Ala Ala Arg Glu
            100                 105                 110

Leu Tyr Leu Gly Ala Cys Arg Gly Asp Val Arg Val Thr Pro Thr Phe
        115                 120                 125

Val Gly Ala Ala Ile Val Gly Leu Val Gly Arg Thr Asp Ala Val Thr
    130                 135                 140

Gly Phe Ser Val Lys Val Leu Thr Phe Ser Ser Pro Thr Ile Val Val
145                 150                 155                 160

Val Gly Leu Asn Gly Met Ser Gly Ile Tyr Lys Val Cys Ile Ala Ala
                165                 170                 175

Thr Ser Gly Asn Val Gly Gly Val Lys Leu Ile Asn Gly Cys Gly Tyr
            180                 185                 190

Phe Asn Thr Pro Leu Arg Phe Asp Asn Phe Gln Gly Gln Ile Tyr Val
        195                 200                 205

Ser Asp Thr Phe Glu Val Arg Gly Thr Lys Asn Lys Cys Val Leu Leu
    210                 215                 220

Arg Ser Ser Ser Asp Thr Pro Leu Cys Ser His Ile Met Arg Asn Val
225                 230                 235                 240

Glu Leu Asp Glu Tyr Val Asp Thr Pro Asn Thr Gly Val Tyr Pro
                245                 250                 255

Ser Asp Gly Phe Asp Ser Leu His Gly Ser Ala Ser Val Arg Thr Phe
            260                 265                 270

Leu Thr Asp Ala Leu Thr Cys Pro Asp Ile Asp Trp Ser Arg Ile Asp
        275                 280                 285

Ala Ala Ser Cys Glu Tyr Asp Ser Cys Pro Lys Met Val Lys Asp Phe
    290                 295                 300

Asp Gln Thr Ser Leu Gly Asn Thr Asp Thr Leu Ile Met Arg Glu Val
305                 310                 315                 320

Ala Leu His Lys Glu Met Ile Ser Lys Leu Gln Arg Asn Ile Thr Asp
                325                 330                 335

Val Lys Ile Arg Val Asp Ala Ile Pro Pro Gln Leu Asn Gln Thr Met
            340                 345                 350

Gly Val Ala Gly Phe Gly Ile Ala Leu Phe Leu Ala Gly Trp Lys Ala
        355                 360                 365

Cys Ile Trp Ile Ala Ala Phe Met Tyr Lys Ser Arg Gly Arg Ile Pro
```

```
                 370                 375                 380
Pro Ser Ser Leu Ser Val Ala
385                 390

<210> SEQ ID NO 4
<211> LENGTH: 29
<212> TYPE: DNA
<213> ORGANISM: Infectious salmon anemia virus

<400> SEQUENCE: 4
gggctagcat ggcacgattc ataatttta                                    29

<210> SEQ ID NO 5
<211> LENGTH: 31
<212> TYPE: DNA
<213> ORGANISM: Infectious salmon anemia virus

<400> SEQUENCE: 5
ggggtaccgt agcaacagac aggctcgatg g                                 31
```